(12) United States Patent
Starkebaum

(10) Patent No.: US 7,043,295 B2
(45) Date of Patent: May 9, 2006

(54) METHODS AND APPARATUS FOR DELIVERING A DRUG INFLUENCING APPETITE FOR TREATMENT OF EATING DISORDERS

(75) Inventor: Warren L. Starkebaum, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 718 days.

(21) Appl. No.: 10/133,251

(22) Filed: Apr. 26, 2002

(65) Prior Publication Data

US 2003/0204181 A1 Oct. 30, 2003

(51) Int. Cl.
*A61B 5/04* (2006.01)
*A61K 9/22* (2006.01)
*A61M 31/00* (2006.01)

(52) U.S. Cl. .................. 600/546; 604/891.1; 604/503; 604/66; 604/67; 607/40

(58) Field of Classification Search .. 604/890.4–891.1, 604/65–66, 503, 67; 600/546; 607/40
See application file for complete search history.

(56) References Cited

U.S. PATENT DOCUMENTS

| | | | |
|---|---|---|---|
| 5,011,472 A | * | 4/1991 | Aebischer et al. ........ 604/892.1 |
| 5,188,104 A | | 2/1993 | Wernicke et al. |
| 5,263,480 A | | 11/1993 | Wernicke et al. |
| 5,290,808 A | | 3/1994 | Sofia |
| 5,423,872 A | | 6/1995 | Cigaina |
| 5,531,787 A | | 7/1996 | Lesinski et al. |
| 5,540,730 A | | 7/1996 | Terry, Jr. et al. |
| 5,571,148 A | | 11/1996 | Loeb et al. |
| 5,603,726 A | | 2/1997 | Schulman et al. |
| 5,643,207 A | | 7/1997 | Rise |

(Continued)

FOREIGN PATENT DOCUMENTS

| WO | WO 99/03533 A1 | 1/1999 |
|---|---|---|
| WO | WO 03/0003791 A1 | 1/2003 |

OTHER PUBLICATIONS

William A. Banks and Carl P. Lebel, "Strategies for the Delivery of Leptin to the CNS", *Journal of Drug Targeting*, 2002 vol. 10 (4), pp. 297-308.

(Continued)

*Primary Examiner*—Mark Bockelman
(74) *Attorney, Agent, or Firm*—Erik Waldkoetter; Thomas F. Woods; Mary P. Bauman

(57) ABSTRACT

Methods and systems for treating patients suffering from eating disorders, e.g. obesity, through the dispensation of a drug by an implantable infusion pump (IIP) delivering drug into the cerebral spinal fluid (CSF) at a site of the intrathecal space in amounts and at times effective to suppress the patient's appetite through interaction of the drug transported through the CSF with receptors in the brain. Delivery of a programmed drug dosage is preferably by one of time-out of programmed time(s) of day, a command received from the patient, or a trigger signal developed from a sensed GI tract signal accompanying peristalsis.

44 Claims, 10 Drawing Sheets

U.S. PATENT DOCUMENTS

| | | | |
|---|---|---|---|
| 5,690,691 | A | 11/1997 | Chen et al. |
| 5,749,912 | A | 5/1998 | Zhang et al. |
| 5,782,798 | A | 7/1998 | Rise |
| 6,115,635 | A | 9/2000 | Bourgeois |
| 6,161,046 | A | 12/2000 | Maniglia et al. |
| 6,327,503 | B1 | 12/2001 | Familoni |

OTHER PUBLICATIONS

G. L. Florant et al., "Intraventricular Insulin Reduces Food Intake and Body Weight of Marmots During the Summer Feeding Period", *Physiology & Behavior*, vol. 49, pp. 335-338, Pergamon Press pic. 1991, USA.

Mark Chavez et al., "Intraventricular Insulin and the Level of Maintained Body Weight in Rats", *Behavioral Neuroscience*, 1995, vol. 109, No. 3, pp. 528-531, American Psychological Association, Inc., 1995, USA.

D. Porte, Jr. et al., "Obesity, diabetes and the central nervous system", *Diabetologia* (1998) 41, pp. 863-881, Springer-Verlag, 1998.

Karl J. Kaiyala et al., "Obesity Induced by a High-Fat Diet is Associated With Reduced Brain Insulin Transport in Dogs", *Diabetes*, vol. 49, Sep. 2000, pp. 1525-1533.

M.W. Schwartz et al., "Insulin in the Brain: A Hormonal Regulator of Energy Balance", *Endocrine Reviews Monographs*, Aug. 1992, vol. 13, No. 3, pp. 387-414.

A.J. Sipols et al., "Effect of Intracerebroventricular Insulin Infusion on Diabetic Hyperphagia and Hypothalamic Heuropeptide Gene Expression", *Diabetes*, Feb. 1995, vol. 44, pp. 147-151.

S.C. Woods et al., "Chronic intracerebroventricular infusion of insulin reduces food intake and body weight of baboons", *Nature*, Nov. 29, 1979, vol. 282, pp. 503-505.

* cited by examiner

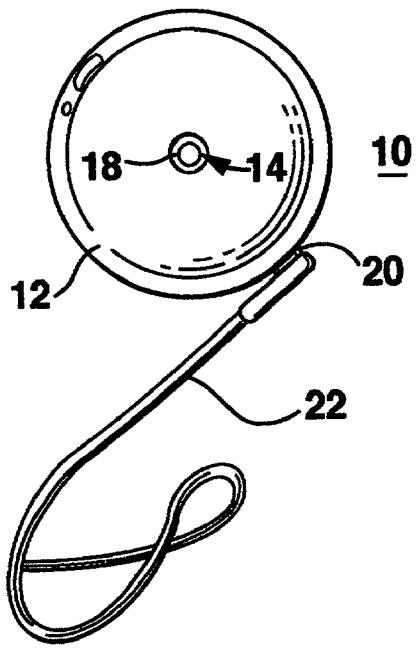
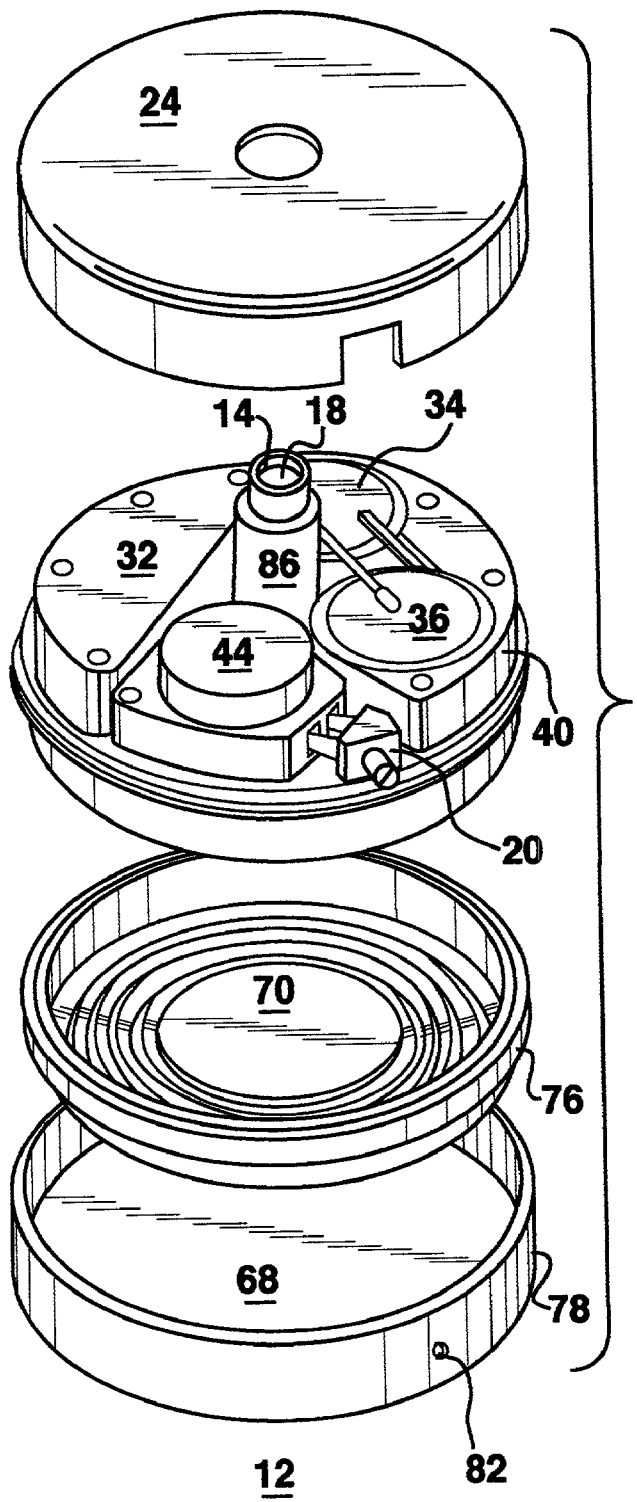
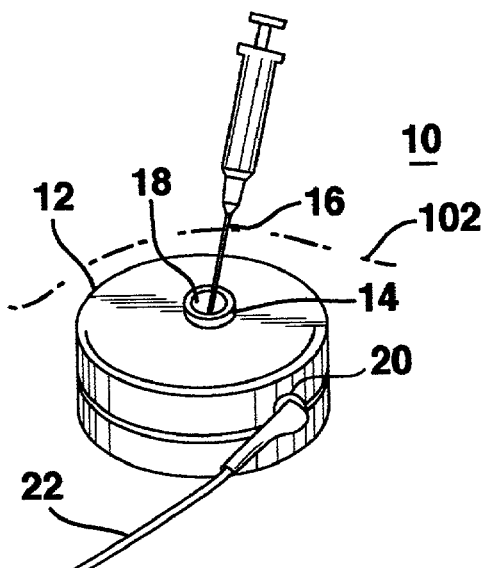

METHODS AND APPARATUS FOR DELIVERING A DRUG INFLUENCING APPETITE FOR TREATMENT OF EATING DISORDERS

FIELD OF THE INVENTION

The present invention pertains to methods and systems for treating patients suffering from eating disorders including obesity or anorexia or the like by dispensing a drug influencing appetite into the cerebral spinal fluid (CSF) at an intrathecal delivery site to interact with receptors in the brain and/or triggering delivery of the drug to detection of GI tract signals indicating stomach emptying.

BACKGROUND OF THE INVENTION

Obesity among adults and children is an increasing problem due generally to increases in caloric intake coupled with declines in exercise levels. Morbid obesity among the same population is also increasing as these habitual tendencies are coupled with physiologic conditions of certain individuals predisposed to obesity that may not fully understood in a given case. The primary treatment has always involved behavorial change involving dietary restraints to reduce caloric intake coupled with aerobic and anaerobic exercise routines or physical therapy regimens to increase caloric expenditure, resulting in a net caloric reduction. Diet and exercise plans fail since most individuals do not have the discipline to adhere to such rigorous discipline. Consequently, the marketplace is flooded with resurrected or new dietary supplements and ethical (or prescription) and patent (or nonprescription) drugs or other ingestible preparations promoted as capable of suppressing appetite or inducing satiety (i.e., the satisfied feeling of being full after eating) or of "burning" fat.

More radical surgical approaches are also commonly employed particularly liposuction (suction lipectomy) for removing adipose tissue from obese patients. Liposuction also enjoys wide application for cosmetic reshaping of the anatomy, particularly the abdomen, hips, thighs and buttocks of non-obese persons. In advanced or extreme cases, treatment of obesity has included more radical techniques such stapling or re-sectioning of the stomach, or wiring the jaws shut.

In general, these and other prior art techniques for treating compulsive overeating/obesity have tended to produce only a temporary effect. The individual usually becomes discouraged and/or depressed in the course of the less radical therapies primarily focused on behavioral change after the initial rate of weight loss plateaus and further weight loss becomes harder to achieve. The individual then typically reverts to the previous behavior of compulsive overeating and/or indolence. And individuals undergoing liposuction and jaw wiring may enjoy their lower weight and bulk for a time, but eventually typically regain the excised or lost weight and volume. The surgical resection of the stomach works well for some individuals, but others experience serious unpleasant side effects that, together with the risk, recuperation pain, and expense of such major surgery, discourage its widespread adoption.

Many other therapies have been proposed, including electrical stimulation of the stomach and/or gut to block stomach emptying and prolong a feeling of satiety as disclosed in U.S. Pat. Nos. 5,423,872 and 5,690,691. It is believed that a satiety center in the brain develops the sensation of satiety in a complicated manner believed in part to be due to increased firing of afferent vagal fibers of the vagal nerves extending between the stomach and brain when the stomach is filled. Thus, it has been proposed to electrically stimulate the stomach or the vagus nerves, as set forth in U.S. Pat. Nos. 5,263,480 and 5,188,104, at a rate mimicking the observed increase to mediate afferent information from the stomach to the satiety centers. Unfortunately, it is not a simple procedure to implant the stomach wall or vagal nerve electrodes, or to do so in an effective place to accomplish the goal of inducing the satiety sensation when the stomach is not actually full. And, the vagal nerves are involved in the regulation of the function of many body organs, including the heart, and stimulation of vagal nerves for any given purpose can have unintended consequences.

Although the blame for weight gain due to the inability to reduce caloric intake and increase caloric expenditure in exercise was historically laid upon the sins of gluttony and sloth, a great deal of evidence has been gleaned from observation and controlled experiments that supports the theory that the body tends to seek and to maintain a body weight in a regulatory manner. Experiments conducted in a wide body of medical research have shown that the body works to regain its previous weight after weight loss due to reduced net caloric input, particularly involving shrinkage of adipose tissue, is achieved by more efficiently rebuilding the adipose tissue, even if net caloric input remains reduced from where it was at the outset. Genetically, the body is predisposed to accumulate adipose stores to forestall famine employing an efficient regulatory system that matches caloric intake to caloric expenditure. Thus, it appears that once the body achieves a historic volume of adipose tissue, the regulatory system works to maintain that historic volume of adipose tissue that it has worked to achieve despite attempts to reduce it through reduced net caloric intake.

It has been postulated that the weight maintaining mechanism is also influenced by insulin that circulates in CSF in the interstitial spaces of the brain which binds with insulin receptors in brain regions known to be involved in the regulation of food intake and body weight. However, it is unclear how insulin enters the CNS, because its molecular size would seemingly prevent insulin in the blood stream from passing through the blood-brain barrier (BBB). It is postulated that the CNS itself may have a limited capacity to synthesize and release insulin locally or that a specialized transport process exists to transport plasma insulin across the BBB. See, for example, the article by M. W. Schwartz et al., "Insulin in the Brain: A Hormonal Regulator of Energy Balance", *Endocrine Reviews Monographs,* August 1992, vol. 13, no. 3, pp. 387–414.

The weight control effects of delivering insulin directly into the brain of the CSF circulating in the brain have been reported in further articles including: (1) M. Chavez et al., "Intraventricular Insulin and the Level of Maintained Body Weight in Rats", *Behavorial Neuroscience,* 1995, Vol. 109, No. 3, pp. 528–531; (2) G. L. Florant et al., "Intraventricular Insulin Reduces Food Intake and Body Weight of Marmots During the Sumer Feeding Period", *Physiology & Behavior,* 1991, Vol. 49, pp. 335–338; (3) A. J. Sipols et al., "Effect of Intracerebroventricular Insulin Infusion on Diabetic Hyperphagia and Hypothalamic Neuropeptide Gene Expression", *Diabetes,* February 1995, Vol. 44, pp. 147–151; and (4) S. C. Woods et al., "Chronic intracerebroventricular infusion of insulin reduces food intake and body weight of baboons", *Nature,* Nov. 29, 1979, Vol. 282, pp. 503–505. The authors report the results of direct infusion of predetermined dosages of insulin at predetermined daily rates into the CSF in the intracerebroventricular spaces around the brain ventricles of rats, marmots or baboons Theoretical explanations of the interactions of a number of drugs or chemicals with receptors in the brain are presented in U.S. Pat. No. 5,290,808. The complex influence of central neurochemical activity on the expression of appetite involves numerous interactions between different loci and different receptors that result in shifts in the magnitude, direction and quality of eating behavior. The '808 patent further states that a great deal of data has been accumulated from the direct application of drugs to specific sites of the brain or the indirect application of drugs to the brain via the CSF which is supported by the above literature citations. Most agents suppress intake but a significant number stimulate eating, sometimes in a dramatic fashion. The most frequently demonstrated action is the stimulation of feeding following activation of $_2$-adrenoceptors in the paraventricular nucleus (PVN). It is also known that spontaneous feeding is associated with endogenous release of noradrenaline in the PVN, and with an increase in PVN $_2$-adrenoceptor density. In turn, it appears that the PVN is a site for the long-established anorexic action of 5-HT receptor agonists. The PVN also contains glucosensitive neurons and therefore may be a point of interaction for neurotransmitter activity and metabolic states reflecting energy regulation. Circulating corticosteroids have been demonstrated to influence $_2$-adrenoceptor sensitivity, and it has been argued that noradrenaline and 5-HT act antagonistically to influence the release of CRF. Since the PVN is also a potent anorectic drug binding site, neurochemical activity in this area may serve to integrate behavioral, metabolic and neuroendocrine responses. In more lateral areas of the hypothalamus (perifornical zone) feeding is suppressed by micro-injection of agents that activate dopamine $D_2$ receptors or $B_2$-adrenoreceptors. Noradrenaline, 5-HT and dopamine consequently produce quantitative shifts in feeding from closely related sites in the hypothalamus.

The '808 patent further states that potent feeding responses can also be obtained by micro-injection of peptides to the brain. Many peptides such as insulin, CCK, calcitonin, bombesin, neurotensin, THRH, somatostatin, VIP, CRF and glucagon suppress feeding after cerebroventricular administration. A smaller number of peptides, including B-endorphin, dynorphin, neuropeptide Y, peptide YY and galanin, increase food intake.

The '808 patent does not propose directly injecting such appetite influencing drugs into the brain or CSF, but instead discloses particular drug dosage forms for oral administration.

An implantable infusion pump (IIP) comprising an implantable pump and catheter is disclosed in commonly assigned U.S. Pat. Nos. 5,643,207 and 5,782,798 for dispensing pancreatic polypeptide blockers and other drugs that decrease sensations of hunger and increase satiety into particular sites in the brain through a distal catheter segment that is implanted through the skull and extends to the specific sites. The delivery of other appetite influencing drugs directly into the brain for increasing appetite to treat anorexia is also proposed in the '207 patent. The drug that is dispensed from the infusion pump coupled to the catheter through the catheter lumen and into the brain is expected to induce or increase the feeling of satiety to treat obesity by reducing caloric intake or to increase feelings of hunger to treat anorexia by increasing caloric intake. The system of the '798 patent can also be employed to apply electrical stimulation to the brain through catheter borne electrodes and conductors to increase feelings of satiety to treat obesity or to decrease feelings of satiety to treat anorexia presumably either with of without delivery of the identified drugs. While these treatments have merit, the implantation of a catheter and stimulation electrodes through a skull entry into the brain is a significant surgical procedure. Also, it is necessary to form a complex catheter and lead preformed with or capable of making a 90° turn at the skull entrance so that the more proximal catheter segment can be tunneled under the scalp, down the neck and to the chest region, where the combined neurostimulator and IIP are implanted.

Obesity is often associated with diabetes, and diabetics inject insulin into their bodies to control its symptoms. In recent years, IIPs have been developed to deliver insulin for patients with diabetes. External pumps deliver insulin into subcutaneous tissue via a percutaneous needle connected to a battery powered external pump worn and controlled by the patient. Implantable battery powered IIPs have also been used to deliver insulin to the peritoneal cavity.

Therapeutic administration of pain suppression or therapeutic drugs into the intraspinal space, that is to either the epidural space or to the intrathecal space, is known. The spinal cord is surrounded by three meningeal sheaths that are continuous with those which encapsulate the brain within the enclosure by the vertebral canal for the spinal cord by the bones of the vertebrae. The outermost of these three meningeal sheaths is the dura matter, a dense, fibrous membrane which anteriorially is separated from the periosteum of the vertebral by the epidural space. Posterior to the dura matter is the subdural space. The subdural space surrounds the second of the three meningeal sheaths, the arachnoid membrane, which surround the spinal cord. The arachnoid membrane is separated from the third meningeal sheath, the pia mater, by the subarachnoid or intrathecal space. The subarachnoid space is filled with CSF. Underlying the pia mater is the spinal cord. Thus the progression proceeding inwards or in posterior manner from the vertebra is the epidural space, dura matter, subdural space, arachnoid membrane, intrathecal space, pia matter and spinal cord.

Administration of a drug directly to the intrathecal space can be by either spinal tap injection or by catheterization. Intrathecal drug administration can avoid the inactivation of some drugs when taken orally as well and the systemic effects of oral or intravenous administration. Additionally, intrathecal administration permits use of an effective dose that is only a fraction of the effective dose required by oral or parenteral administration. Furthermore, the intrathecal space is generally wide enough to accommodate a small catheter, thereby enabling chronic drug delivery systems. Thus, it is known to treat spasticity by intrathecal administration of baclofen. Additionally, it is known to combine intrathecal administration of baclofen with intramuscular injections of botulinum toxin for the adjunct effect of intramuscular botulinum for reduced muscle spasticity. Furthermore, it is known to treat pain by intraspinal administration of the opioids morphine and fentanyl.

The current method for intrathecal treatment of chronic pain is by use of an intrathecal IIP, such as the SynchroMed® Infusion System, a programmable, implanted pump available from Medtronic, Inc., of Minneapolis, Minn. A pump is required because the antinociceptive or antispasmodic drugs in current use have a short duration of activity and must therefore be frequently re-administered, which re-administration is not practically carried out by daily spinal tap injections. The pump is surgically placed under the skin of the patient's abdomen. One end of a catheter is connected to the pump, and the other end of the catheter is threaded into a CSF filled subarachnoid or intrathecal space in the patient's spinal cord. The implanted pump can be programmed for continuous or intermittent infusion of the drug through the intrathecally located catheter.

SUMMARY OF THE INVENTION

A first aspect of the invention involves delivery of a drug for treating an eating disorder into the CSF in the intrathecal space that circulates through the CNS to reach receptors in the brain controlling appetite. Delivery of a programmed drug dosage is preferably by one of time-out of programmed time(s) of day, or a command received from the patient.

A second aspect of the invention involves triggering the delivery of such drugs into the CSF in the intrathecal space or into the intercerebroventricular space of the brain to reach receptors in the brain controlling appetite conditioned upon the detection of certain GI tract signals, particularly spike potentials characteristic of peristalsis. The GI tract signals can be detected by GI tract leads and electrodes and a GI tract signal sense amplifier integrated into an IIP. Or a separate GI tract signal monitor/stimulator and associated GI tract leads can be implanted in the patient, and telemetry transmissions can be established between the separate IIP and GI tract monitor/stimulator.

The drug dosages and other operating modes and parameters of the GI tract monitor/stimulator and/or the IIP can be programmed by the physician following the patient. A programmable delay timer is preferably timed out from an earlier delivery of a drug dosage to limit frequent deliveries of the programmed drug The present invention can be employed to deliver any of the above identified drugs into the CSF to suppress appetite and/or increase feelings of satiety in obese patients or to deliver other of the above-identified drugs into the CSF to increase appetite and/or decrease feelings of satiety in patients having other eating disorders.

One preferred use of the present invention is to deliver dosages of insulin acting to suppress appetite when detected by the receptors in the brain. The dosage of insulin can be in the range of $1 \times 10^{-5}$–$15 \times 10^{-2}$ Units/Kg/day.

The present invention is preferably embodied in an IIP that delivers a drug into the CSF in the intrathecal space to increase the concentration of the drug in the CSF that circulates to the receptors in the brain that respond by decreasing feelings of hunger and/or increasing the sensation of satiety to treat obesity or that respond by increasing feelings of hunger and/or decreasing the sensation of satiety to treat anorexia.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, wherein:

FIG. 1 is a diagrammatic view of a preferred form of an IIP and intrathecal drug delivery catheter implanted beneath skin (shown in phantom) with a reservoir of the IIP being filled with an appetite influencing drug by a hypodermic syringe;

FIG. 2 is a plan view of the IIP and intrathecal drug delivery catheter shown in FIG. 1;

FIG. 3 is an exploded view of the IIP shown in FIG. 1 with the intrathecal drug delivery catheter removed;

DETAILED DESCRIPTION OF THE PREFERRED EMBODIMENTS

In the following detailed description, references are made to illustrative embodiments for carrying out various aspects of the invention. A first aspect of the invention involves delivery of a drug for treating an eating disorder into the CSF in the intrathecal space that circulates through the CNS to reach receptors in the brain controlling appetite. Exemplary embodiments of the first aspect of the invention involving the delivery of the drug, particularly insulin, into the intrathecal space by an IIP under various conditions are depicted in FIGS. 1–13 and described as follows. The disclosed embodiments can also be employed to deliver other drugs identified above into the CSF in the intrathecal space to suppress appetite and/or increase feelings of satiety in obese patients or to deliver other drugs identified above into the CSF in the intrathecal space to increase appetite and/or decrease feelings of satiety in patients having other eating disorders.

A second aspect of the invention involves triggering the delivery of such drugs into the CSF in the intrathecal space or into the intercerebroventricular space of the brain to reach receptors in the brain controlling appetite conditioned upon the detection of certain GI tract signals, particularly spike potentials characteristic of peristalsis, as depicted particularly in FIGS. 8–14 and described as follows.

It is further intended that other embodiments than the specifically described embodiments can be utilized without departing from the scope of the invention.

Figure 5:
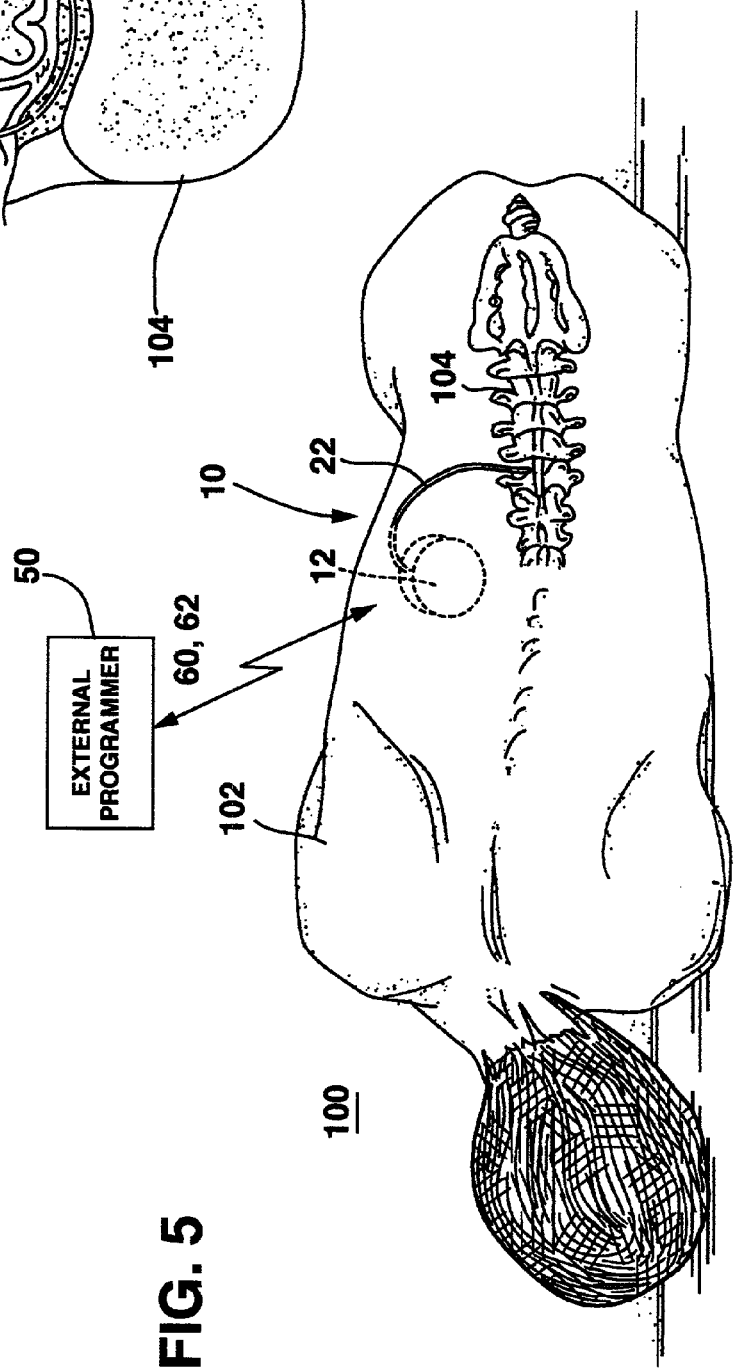
FIG. 5 schematically depicts the IIP of FIG. 4 implanted in accordance with the first aspect of the invention so that the intrathecal drug delivery catheter extends into the intrathecal space and an external programmer for programming operating modes and parameters of the IIP for controlling the operation of the IIP.

Referring to FIGS. 1 and 2, an IIP 10 in which the present invention can be practiced is shown implanted below a layer of skin 102 (indicated in phantom). The IIP 10 comprises the subcutaneous pump 12 and an intrathecal insulin infusion catheter 22 coupled with subcutaneous pump 12. The pump 12 is formed with a port 14 into which a hypodermic needle 16 can be inserted through the skin 102 to inject a quantity of liquefied insulin through a septum 18 into a drug reservoir located within the housing of subcutaneous pump 12. The liquid insulin is pumped from subcutaneous pump 12 through the lumen of an intrathecal insulin infusion catheter 22 attached to the catheter port 20. The intrathecal insulin infusion catheter 22 is surgically implanted to deliver the insulin into the intrathecal space, particularly into the intrathecal space, as shown in FIG. 5.

FIG. 3 depicts the major components of the subcutaneous pump 12 that include an upper housing 24, a control module 40, a bellows 76 and a lower housing 78. A drug reservoir 70 is formed between the upper surface of the bellows 76 and the lower surface of module 40, and a pressure chamber 68 is formed below the bellows 76 and the lower housing 78. When the components are sealed together, the pressure chamber 68 is filled with a fluorocarbon through port 82 that is then sealed so that the bellows 76 exerts a constant force against any volume of insulin that is injected into the drug reservoir 70.

Figure 4:
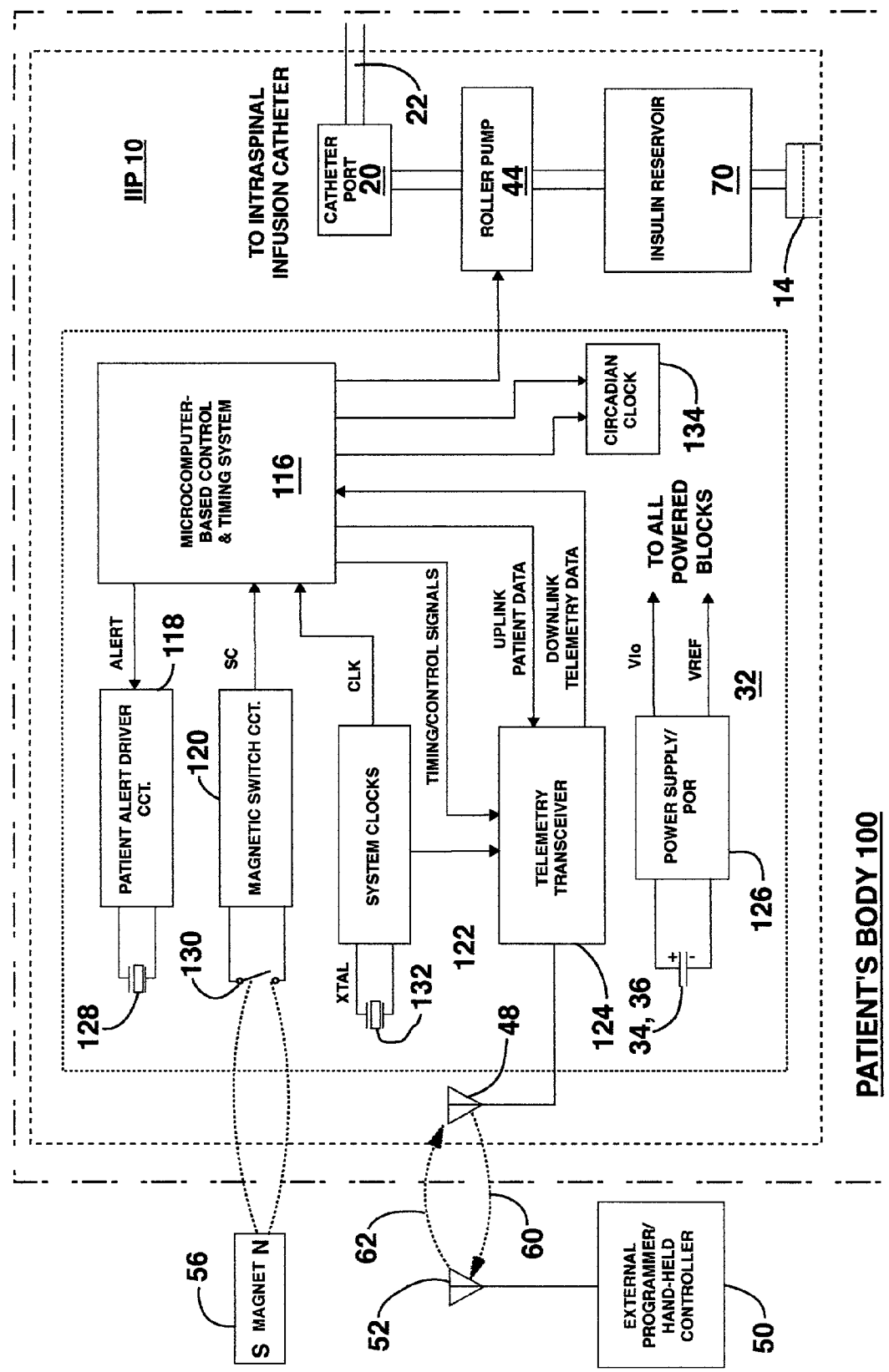
FIG. 4 is a block diagram of the components of the IIP of FIGS. 1–3 in relation to an external programmer for programming operating modes and parameters of the IIP for controlling operations of the IIP.

The control module 40 supports a telemetry antenna 48 and batteries 34 and 36 that power a peristaltic roller pump 44 coupled between the reservoir and the catheter port 20 and circuitry within the electronic circuit module 32 that is depicted in the block diagram of FIG. 4. The peristaltic roller pump 44 includes a motor that drives a gear train, which in turn drives a shaft that is connected to an arm that supports a pair of rollers. The details of the construction and operation of the roller pump 44 are not important to the present invention. An exemplary roller pump 44 can be found depicted and further described in the above-referenced, commonly assigned '207 patent.

The drug reservoir 70 is filled with insulin using the hypodermic needle 16 by inserting the hypodermic needle through the patient's skin 102 and then through the resealable membrane 18 of port 14 and into neck 86 as described in the above-referenced '990 patent. The roller pump 44 is operated as described further below to pump a bolus or dosage of insulin from the reservoir 70 through the insulin infusion lumen of the intrathecal insulin infusion catheter 22 into the intrathecal space. The catheter 22 can be of the type described in the above-referenced '990 patent.

A block diagram of one embodiment of the IIP 10 implanted within a patient's body 100 and in communication with an external programmer 50 and an externally applied magnet 56 is depicted in FIG. 4. The IIP 10 has a system architecture that is constructed about a microcomputer-based control and timing system 116 that varies in sophistication and complexity depending upon the type and functional features incorporated therein. The functions of microcomputer-based IIP control and timing system 116 are controlled by firmware and programmed software algorithms stored in RAM and ROM including PROM and EEPROM and are carried out using a CPU, ALU, etc., of a typical microprocessor core architecture.

Power levels and signals are derived by the power supply/POR circuit 126 having power-on-reset (POR) capability from batteries 34, 36 to power the roller pump 44 and the other components of the circuit module 32. The power supply/POR circuit 126 provides one or more low voltage power Vlo and one or more VREF sources. Not all of the conventional interconnections of these voltage sources and signals with the IIP circuitry are shown in FIG. 4.

Virtually all current electronic IMD circuitry employs clocked CMOS digital logic ICs that require a clock signal CLK provided by a piezoelectric crystal 132 and system clock 122 coupled thereto. In FIG. 4, each CLK signal generated by system clock 122 is routed to all applicable clocked logic of the microcomputer-based control and timing system 116 and to the telemetry transceiver I/O circuit 124. The system clock 122 provides one or more fixed frequency CLK signal that is independent of the battery voltage over an operating battery voltage range for system timing and control functions and in formatting uplink telemetry signal transmissions in the telemetry I/O circuit 124.

In certain IIPs, an audible patient alert warning or message can be generated by a transducer 128 when driven by a patient alert driver 118 to advise of device operations, e.g., confirmed delivery of a bolus or dosage of insulin, or the battery depletion level to warn of a depleted battery state.

In addition, a real-time or circadian clock 134 is included in the circuit module 32 driven by system clocks 122 that provides a time of day signal to the microcomputer-based timing and control system 116.

In the IIP 10, uplink and downlink telemetry capabilities are provided to enable communication with either a remotely located external medical device or programmer 50 or a more proximal medical device on the patient's body or another IMD in the patient's body. For convenience of description, the preferred embodiments are described as follows using RF downlink telemetry (DT) transmissions 62 and uplink telemetry (UT) transmissions 60. The terms "telemeter", "telemetry transmission" and the like are intended to embrace any action and manner of communicating and conveying patient data and downlink telemetry data between the IIP 10 and any external monitoring device or programmer 50 in the UT direction and the DT direction, respectively.

In an uplink telemetry transmission 60, the external RF telemetry antenna 52 operates as a telemetry receiver antenna, and the IIP RF telemetry antenna 48 operates as a telemetry transmitter antenna. Conversely, in a downlink telemetry transmission 62, the external RF telemetry antenna 52 operates as a telemetry transmitter antenna, and the IIP RF telemetry antenna 48 operates as a telemetry receiver antenna.

In general terms, the operation of the roller pump 44 can controlled through resident software and firmware in the microcomputer-based control and timing system 116 in a general manner similar to that described in commonly assigned U.S. Pat. No. 4,692,147. The frequency and volume of each bolus or dosage of insulin delivered into the intrathecal space can be governed by DT transmitted commands that are stored in RAM. Data related to the delivery of insulin can be stored in RAM and uplink telemetry transmitted to the programmer in a telemetry session initiated by a medical care provider.

The circuit module 32 of the implantable pump 12 of IIP 10 may also include a magnetic field sensor or reed switch 130 and a magnetic switch circuit 120 that develops a switch closed (SC) signal when the switch 128 or other magnetic field sensor responds to an externally applied magnetic field. As a safety feature, current telemetry transmission schemes require the application of a magnetic field to generate the SC signal to enable UT transmission from telemetry transceiver 124 and receipt of DT telemetry commands. But, this requirement is being phased out in favor of high frequency telemetry schemes that can function at greater distances between antennas 52 and 48 and do not employ the magnetic field confirmation of a telemetry session. Such a telemetry scheme is preferably used in the embodiments of the present invention to enable alternative use of the magnet 56 and to enable telemetry communications between the IIP 10 and other implantable medical devices implanted in the body 100.

Therefore, in accordance with one aspect of the present invention, a motivated and competent patient is provided with a magnet 56 that can be applied over the subcutaneously implanted IIP 10 to close switch 130 and prompt of command the control and timing system 116 to deliver a bolus or dosage of insulin when the patient experiences hunger pangs or preceding a meal taken by the patient. Alternatively, the patient could be supplied with a limited function programmer or hand-held controller 50 that the patient could employ to generate a DT transmitted command that is received and triggers the delivery of a bolus or dosage of insulin when the patient experiences hunger pangs or preceding a meal taken by the patient.

The frequency of delivery or discharge of dosages of insulin can be limited within a delivery delay time window started by any delivery initiated in either of these ways by the patient. In other words, the receipt of a command from the hand-held controller 50 or closure of switch 130 would initiate delivery of the bolus of insulin and also start a delivery delay timer that would have to time out before the control and timing system 116 can respond to any further commands initiated by the patient's use of the magnet 56 or hand-held controller 50.

The delivery of insulin into the CSF is alternatively controlled in a variety of other ways in accordance with various aspects of the invention as described further herein.

Figure 6:
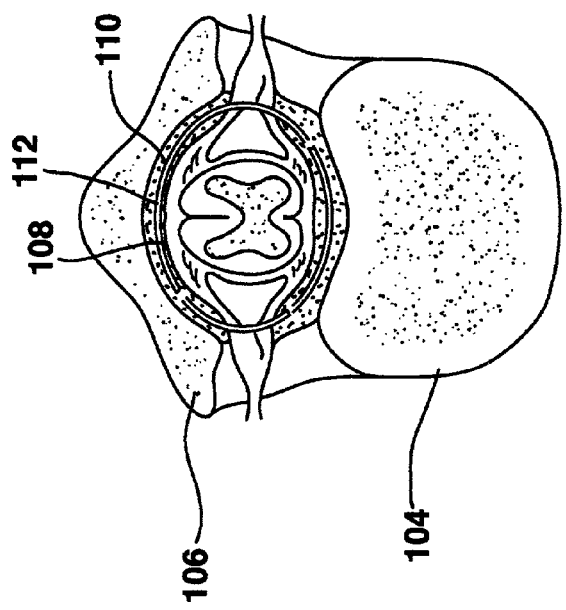
FIG. 6 is a cross-section view of the spinal column depicting the preferred intrathecal spaces for delivery of insulin to treat obesity or other appetite influencing drugs to treat eating disorders in accordance with the invention.

FIGS. 5 and 6 depict an implantation of the IIP 10 in a patient's body 100 with the insulin infusion catheter 22 extending into an intrathecal space in the spinal column 104. FIG. 5 shows the general placement of catheter 22 and infusion pump 12 in relation to the body 100. FIG. 6 is a cross-sectional view of the spinal column 104 of the body 100 that shows some potential infusion sites. As noted above, the spinal cord is surrounded by three meningeal sheaths, which are continuous with those that encapsulate the brain, within the enclosure by the vertebral canal for the spinal cord by the bones of the vertebrae. The outermost of these three meningeal sheaths is the dura matter, a dense, fibrous membrane which anteriorally is separated from the periosteum of the vertebral by the epidural space 110. Posterior to the dura matter is the subdural space. The subdural space surrounds the second of the three meningeal sheaths that surround the spinal cord, the arachnoid membrane. The arachnoid membrane is separated from the third meningeal sheath, the pia mater, by the subarachnoid or intrathecal space 108 that is filled with CSF. The spinal cord underlies the pia mater.

In FIGS. 5 and 6, the distal end of the catheter 22 is obscured by vertebrae. It will be understood that the distal end of the catheter 22 including the distal end opening(s) of the catheter lumen is passed through the arachnoid membrane 112. The infusion pump 12 is surgically implanted subcutaneously in the abdominal region of the body 100. The insulin infusion catheter 22 is tunneled subcutaneously with a distal portion thereof extending between vertebrae 106 and the catheter distal tip lodged in a selected intrathecal space 108 to infuse the bolus or dosage of insulin into the CSF therein. The CSF circulates throughout the CNS and therefore circulates into the intracerebroventricular space into operative proximity with receptors in the brain that are influenced by insulin and that cause feelings of satiety in the manner described in the above-referenced articles.

There are a number of ways that the IIP 10 can employed to dispense insulin into the CSF in accordance with the first aspect of the invention. First, a fixed amount or bolus or dosage can be dispensed at predetermined timed intervals over the entire 24 hour day, that is once a day or more than once a day to maintain a relatively uniform level of insulin in the CSF. Or, a bolus or dosage of insulin may be delivered at the patient's indicated mealtimes as timed out by the circadian clock 134. The patient can also be provided with the magnet 56 or hand-held controller 50 to separately initiate delivery of a dosage by IIP 10 if the delivery delay has timed out. The patient's physician would develop a conservative delivery regimen and use the programmer 50 to DT transmit the delivery times or delivery delay and bolus or dosage quantities. The eating habits and body weight of the patient would be monitored, and the physician would periodically adjust the bolus or dosage depending upon the observed response or lack of response. It would be possible to periodically invasively draw a sample the CSF from the intrathecal space and measure the level of insulin in the CSF.

Figure 7:
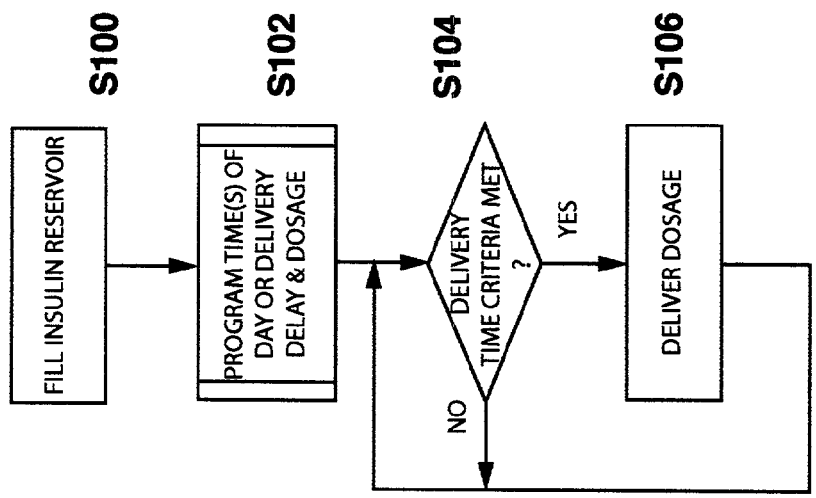
FIG. 7 is a flow chart illustrating the operation of the IIP to dispense a bolus or dosage of insulin to treat obesity or other appetite influencing drugs to treat eating disorders at predetermined times of day or after time-out of a delay time from delivery of a preceding dosage.

FIG. 7 is a flow chart illustrating the operation of the IIP 10 to dispense a bolus or dosage of insulin at predetermined time(s) of day or upon time out of a delivery delay time, which are programmed by the physician following the patient. In step S100, the insulin reservoir 70 is filled. In step S102, the bolus or dosage amounts and the times of day or delivery delay between allowed dosages are programmed taking the weight, age and general health of the patient into account. It is postulated from the above-cited animal studies that a dosage in the range of $1 \times 10^{-4}$ to $15 \times 10^{-2}$ Units/Kg/ day would suffice as a starting dosage to be adjusted as the patient's health, side effects, and weight are monitored.

Returning to FIG. 4, the real time clock is polled in Step S104. The bolus or dosage is delivered in step S106 when the programmed time or times of day occur.

The dosages that have been used in the animal studies cited above and shown to have an effect of food intake or animal body weight are as follows:

| Woods, 1979 | Baboon model | $1 \times 10^{-5} - 1 \times 10^{-4}$ Units/Kg/day |
| Florant, 1991 | Marmot model | $5 \times 10^{-3}$ Units/Kg/day |
| Chavez, 1995 | Rat model | $15 \times 10^{-3}$ Units/Kg/day |
| Sipols, 1995 | Rat model | $8 \times 10^{-3}$ Units/Kg/day |

Normally, U100 insulin is used clinically and in insulin pumps, wherein "U100" means 100 "units" of insulin per cc. Assuming a patient with a body weight of 150 Kg, the dosage range extrapolated from the reported animal studies is:

Low end: $150 \times (1 \times 10^{-5}) = 0.0015$ units/day

High end: $150 \times (15 \times 10^{-3}) = 2.25$ units/day

The low end the volume is quite small in relation to the minimum bolus of fluid that the IIP can eject. Consequently, it may be necessary to dilute the insulin loaded into the IIP reservoir, perhaps 10:1 or 100:1 to stay within the daily volumetric range.

In accordance with the second aspect of the invention, the electrical signals of the GI tract are monitored to ascertain if the patient's stomach is emptying signifying the onset of hunger feelings. Stomach emptying can be detected from characteristic electrical signals accompanying stomach contractions, referred to as peristalsis, moving stomach contents into the intestinal tract. Feelings of hunger follow stomach emptying, and the second aspect of the invention triggers delivery of a drug to counter such feelings to treat obesity or enhance such feelings to treat anorexia or other eating disorders.

The GI tract is responsible for an essential step in the digestive process, the reception of nutrition in the human body. Nutrition is received by absorbing mucosa in the gastrointestinal tract, using a very complex mechanism. An important element of the digestive process is intestinal peristalsis, the coordinated and self-regulated motor activity of the intestinal tract. Peristalsis is accomplished through a coordinated combination of electrical, chemical, and hormonal mediation, possibly in addition to other unknown mechanisms.

Figure 13:
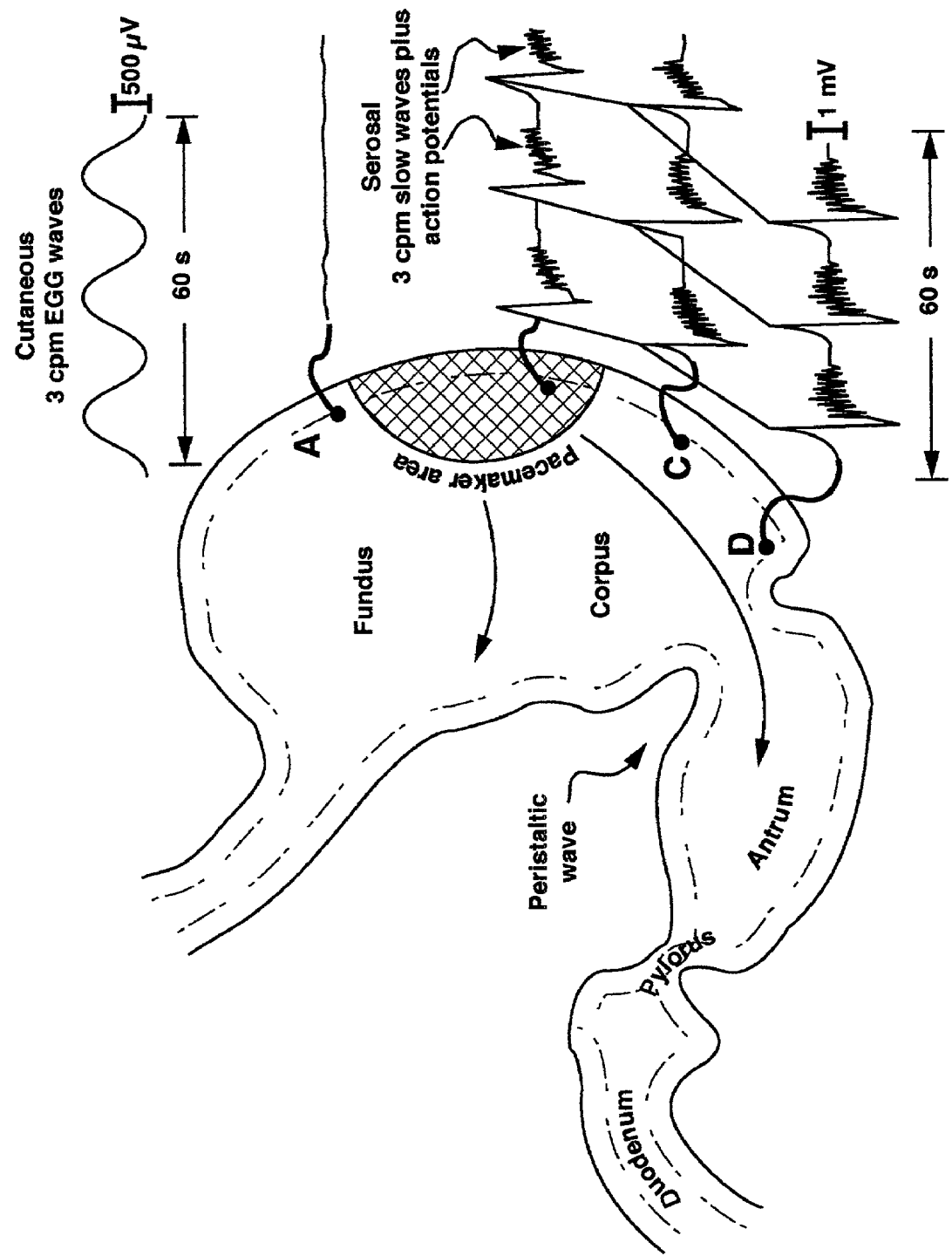
FIG. 13 depicts an example of GI tract signals traversing the stomach wall that can be detected through electrodes coupled to the stomach wall. particularly spike potentials characteristic of peristalsis.
Figure 14:
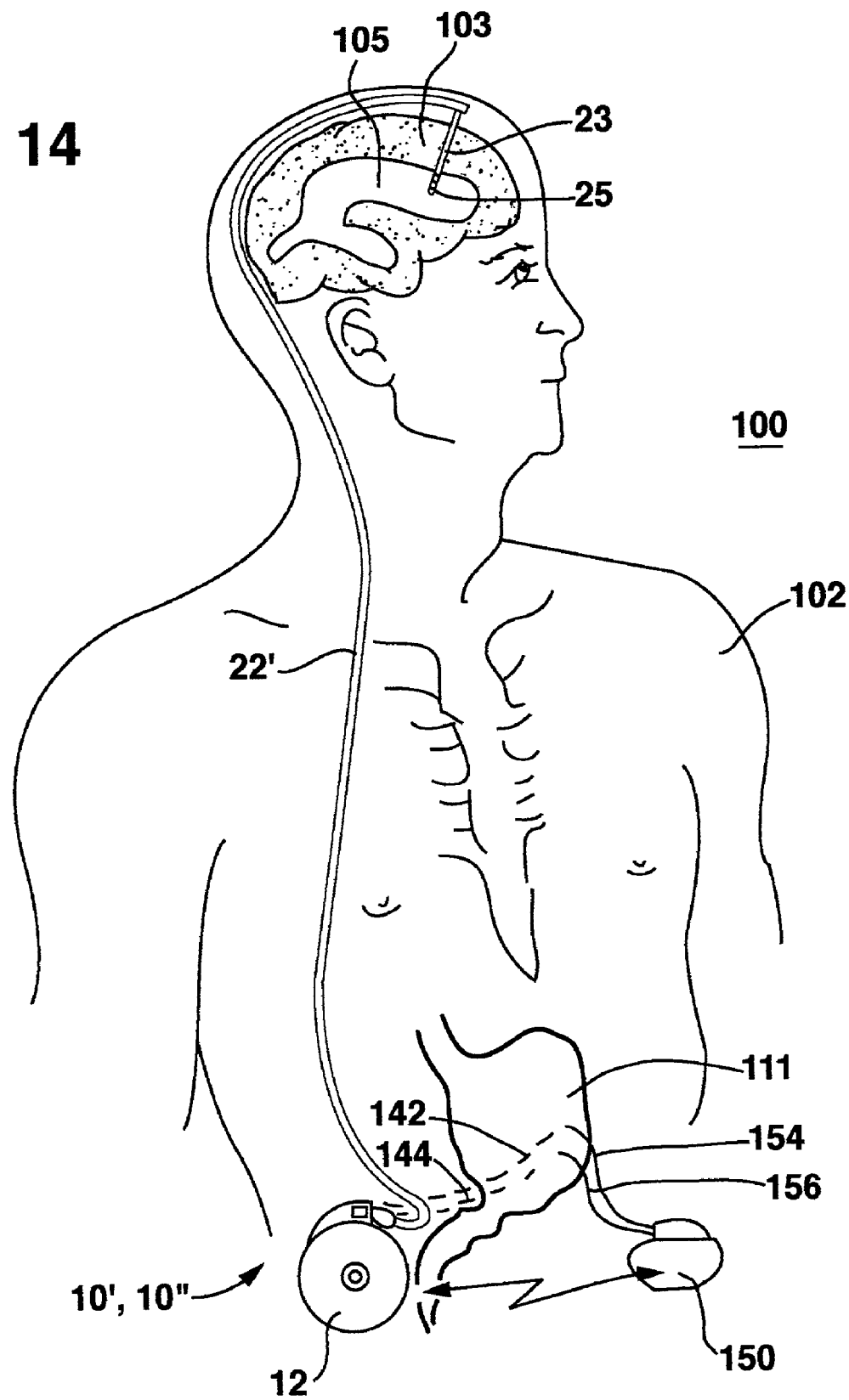
FIG. 14 schematically depicts the implantation and operation of an IIP delivering insulin to treat obesity or other appetite influencing drugs to treat eating disorders directly into the intracerebroventricular space when triggered to do so in accordance with the second aspect of the invention.

As illustrated in FIG. 13, electrogastrogram (EGG) signals that cause the peristaltic contraction of the stomach wall normally originate in the putative pacemaker region near the junction of the proximal one third and the distal two thirds of the gastric body along the greater curvature. The EGG signals include slow waves that normally appear every 10–30 seconds or at a frequency of 2–6 cycles per minute (cpm) and propagate along the stomach wall in a characteristic pattern down to the corpus and pyloric antrim. The slow waves cause the stomach wall to rhythmically contract and move food remaining in the stomach toward the duodenum. The peristaltic contraction functions to both force contents of the stomach into the duodenum as well as to create shear on the stomach contents and thus break the contents down into smaller particles. For example, 3 cpm slow waves are illustrated in FIG. 13 that can be sensed at three locations B, C, D but are not sensed at location A as long as the stomach is functioning normally. The three sensed EGG signals at locations B, C, D exhibit normal timed synchronization.

During a peristaltic contraction, the slow waves further feature a higher voltage, high frequency action or spike potential. As seen, each slow wave features a corresponding high frequency action potential shortly thereafter. The slow waves, as discussed above, typically have a frequency of 3 per minute. The higher frequency action potentials, however, typically have a frequency of between 100–300 Hz. Thus this aspect of the present invention is directed to sensing both the slow waves and the higher frequency fast waves which follow and processing the sensed waves to indicate the state of the stomach at that moment. This is especially useful to thereby determine or detect the presence or absence of peristaltic contraction within the stomach.

EGG sense amplifiers of the type described in commonly assigned U.S. Pat. No. 6,083,249, for example coupled to sense electrodes at one or more of the locations B, C, D in the manner described therein can differentiate between the slow waves and the spike potentials. Thus, it is possible to sense spike activity characteristic of peristalsis and generate a spike sense event on detection of each spike potential. The amplitude and frequency detection thresholds of such sense amplifiers are programmable and can be adjusted to the particular characteristics of the spike potentials in a given patient in a manner well known in the art and the cardiac pacing art.

Figure 8:
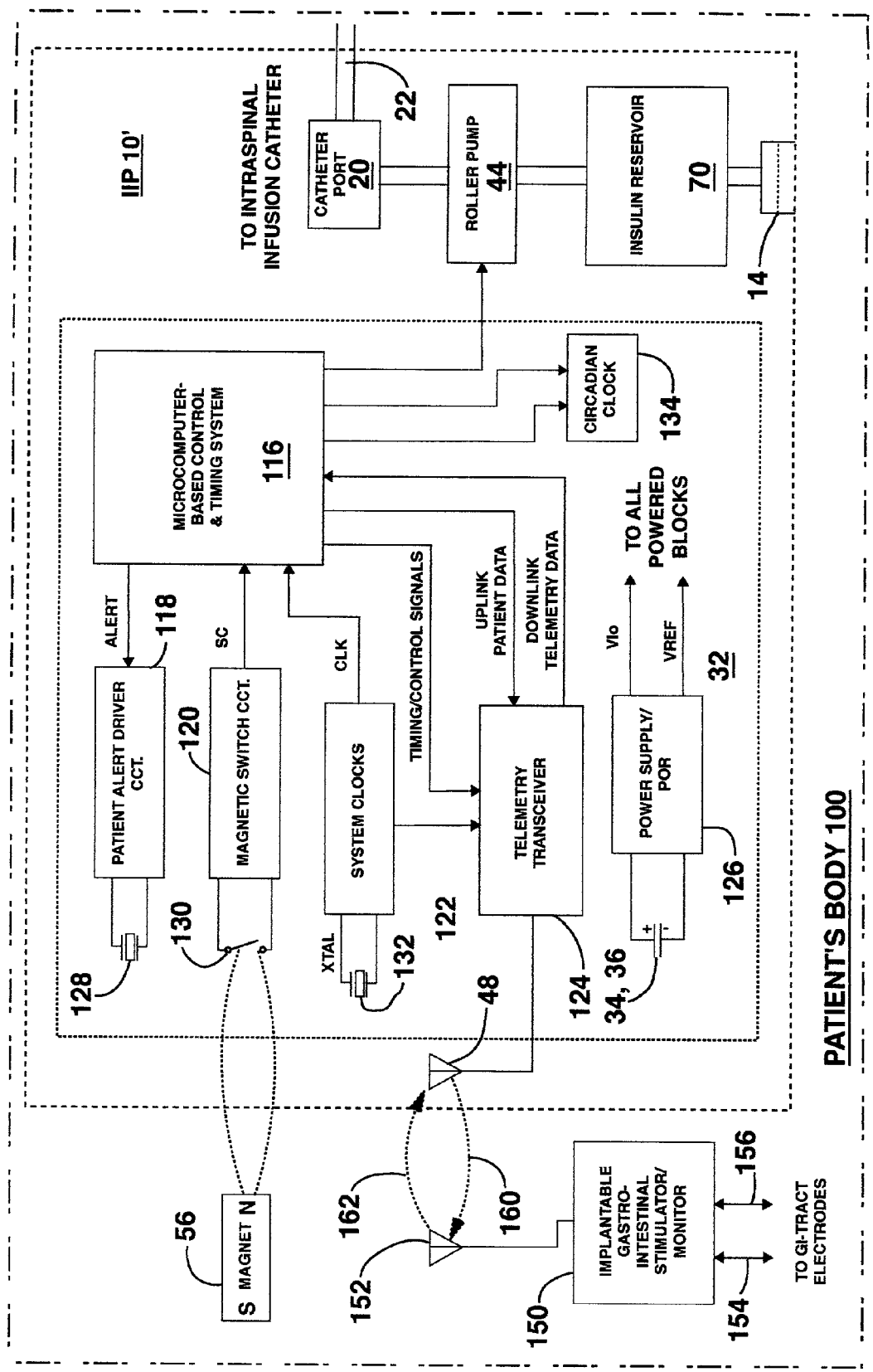
FIG. 8 is a block diagram of the components of the IIP of FIGS. 1–4 in relation to a further implanted gastro-intestinal stimulator/monitor for developing a GI tract signal characteristic of peristalsis that triggers, in accordance with the second aspect of the invention, delivery of a drug into the intrathecal space by the IIP in accordance with the first aspect of the invention.
Figure 9:
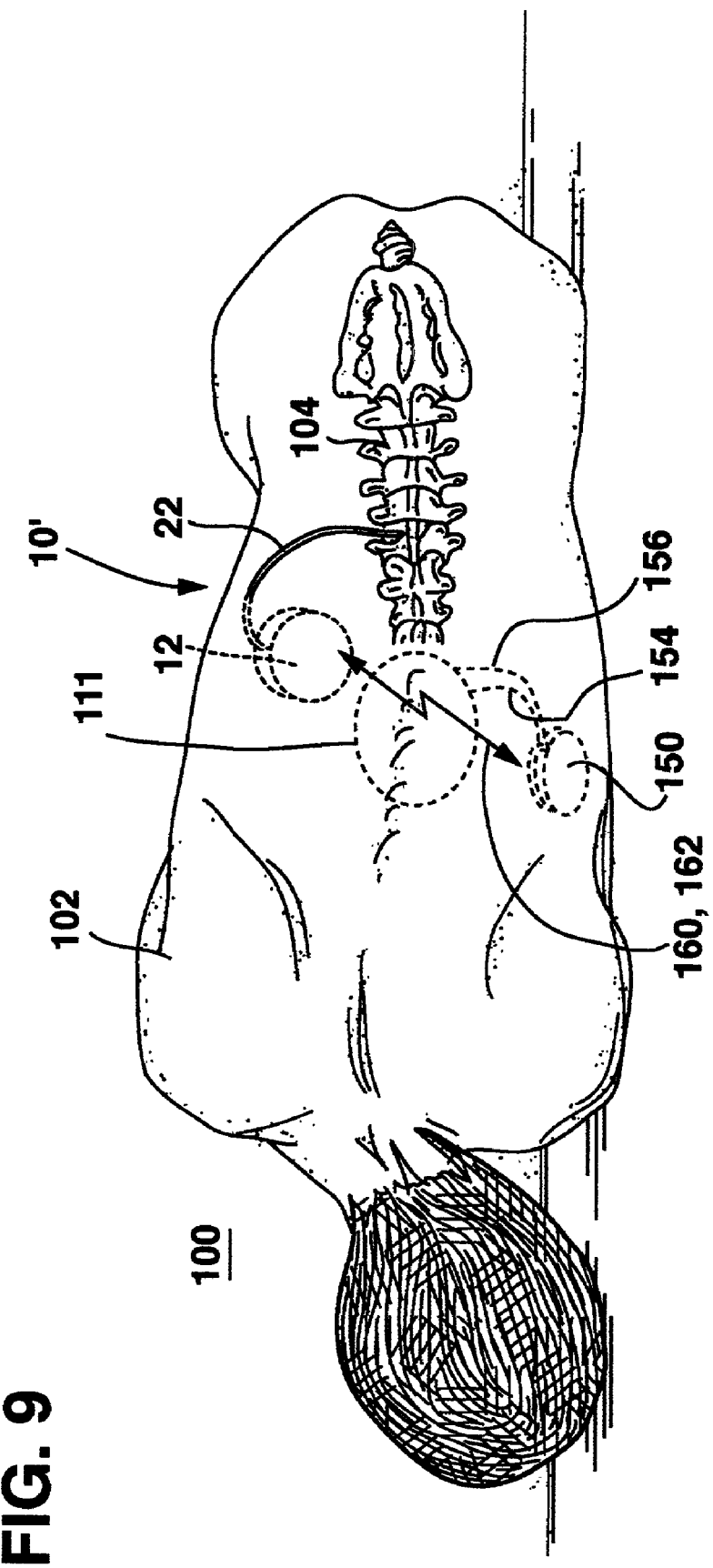
FIG. 9 schematically depicts the IIP of FIG. 8 implanted so that the intrathecal insulin delivery catheter extends into the intrathecal space and the implanted gastrointestinal stimulator/monitor develops and telemetry transmits the GI tract signal to the IIP.

FIGS. 8 and 9 depict the implantation of a GI tract stimulator/monitor 150 and associated GI tract leads 154, 156 extending to GI tract sense electrodes implanted in the wall of stomach 111 having sense amplifiers of the type described in the above-referenced '249 patent developing a GI tract signal upon detection of such spike potentials characteristic of peristalsis. The IIP 10' is structurally the same as IIP 10 of FIG. 4 but communicates by telemetry transmissions with the external programmer 50 of FIG. 4 and through transmissions 160 and 162 between telemetry antennas 152 and 48 with the GI tract stimulator/monitor 150. The operating modes and parameter values of the GI tract stimulator/monitor 150 are also programmable by the external programmer 50. The GI tract stimulator/monitor 150 can also be programmed to monitor GI tract signals for diagnostic purposes and to deliver GI tract stimulation following stimulation regimens for treatment of the patient's eating disorder.

In use, sense amplifiers in the GI tract stimulator/monitor 150 sense the slow wave signals and spike potentials depicted in FIG. 13 and described above and develops the GI tract signal that is telemetry transmitted in telemetry transmission 160 and received and decoded in telemetry transceiver 124. The bolus of insulin is delivered in the manner described above with respect to FIG. 4 if a delivery delay time between deliveries of each bolus has timed out. The delivery delay time can be programmed into memory of and timed out either in the IIP 10' or in the GI tract stimulator/monitor 150 by the physician based upon observation of the patient. In the latter case, the sensing function of the GI tract stimulator/monitor 150 can be disabled during the delivery delay time to conserve energy.

Figure 12:
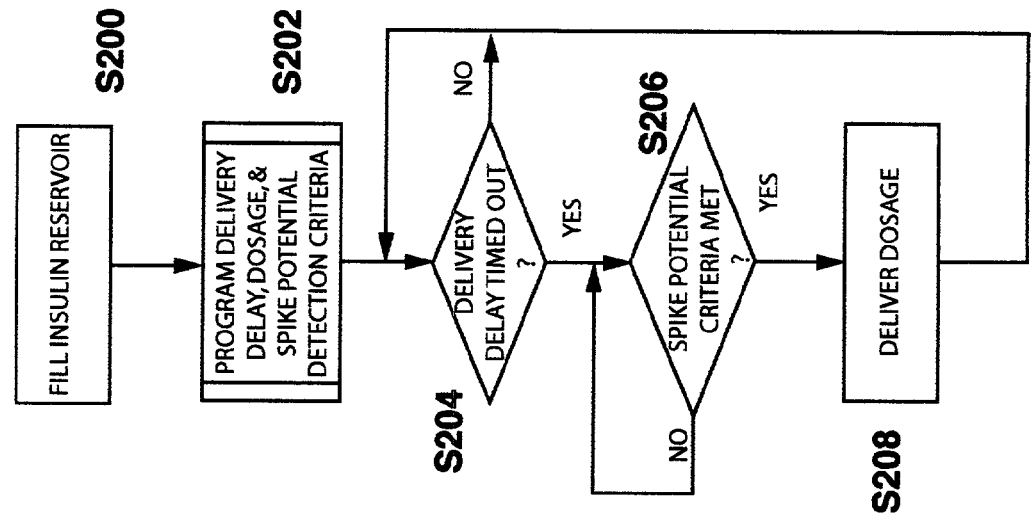
FIG. 12 is a flow chart illustrating the steps of delivering a bolus or dosage of a drug following time-out of a delivery delay and in response to a control signal developed from a directly sensed GI tract signal or a telemetry transmitted GI tract signal.

These cooperative functions of the GI tract stimulator/monitor 150 and the IIP 10' are depicted in FIG. 12. The insulin reservoir 70 is periodically filled in step S200 of FIG. 12 as described above. The gastric signal detection threshold parameters of the sense amplifier of the GI tract stimulator/monitor 150 are programmed in step S202 employing the external programmer 50 of FIG. 4. Similarly, the bolus quantity of insulin to be delivered from insulin reservoir 70 is programmed in step S202 employing the external programmer 50 of FIG. 4 communicating with telemetry transceiver 124 as described above. The delivery delay time between deliveries of each dosage of insulin is also programmed into memory of either of the GI tract stimulator/ monitor 150 and the IIP 10' in step S202 to be timed out in step S204. The delivery delay time must time out in step S204 so that only a single dosage is delivered when peristalsis is detected, and so that dosages are separated in time by the programmed minimum delivery delay time to avoid delivering the insulin dosage too frequently.

During chronic implantation, the GI tract signal is generated and transmitted by GI tract stimulator/monitor 150 in step S206 when the spike potential detection criteria are met and after lapse of the delivery delay time as determined in step S204 if the delivery delay time is timed out by the GI tract stimulator/monitor 150. Or, the GI tract signal that is generated and transmitted by GI tract stimulator/monitor 150 when the spike potential detection criteria are met is processed by the IIP 10' in step S206 only after lapse of the delivery delay time if the delivery delay time is timed out by the IIP 10'. In either case, the insulin dosage is delivered in step S208 once both conditions of steps S204 and S206 are met. Microcomputer-based control and timing system 116 commands roller pump 44 to eject a dosage of insulin through catheter port 20 and catheter 22 into the intrathecal space as described above.

Figure 10:
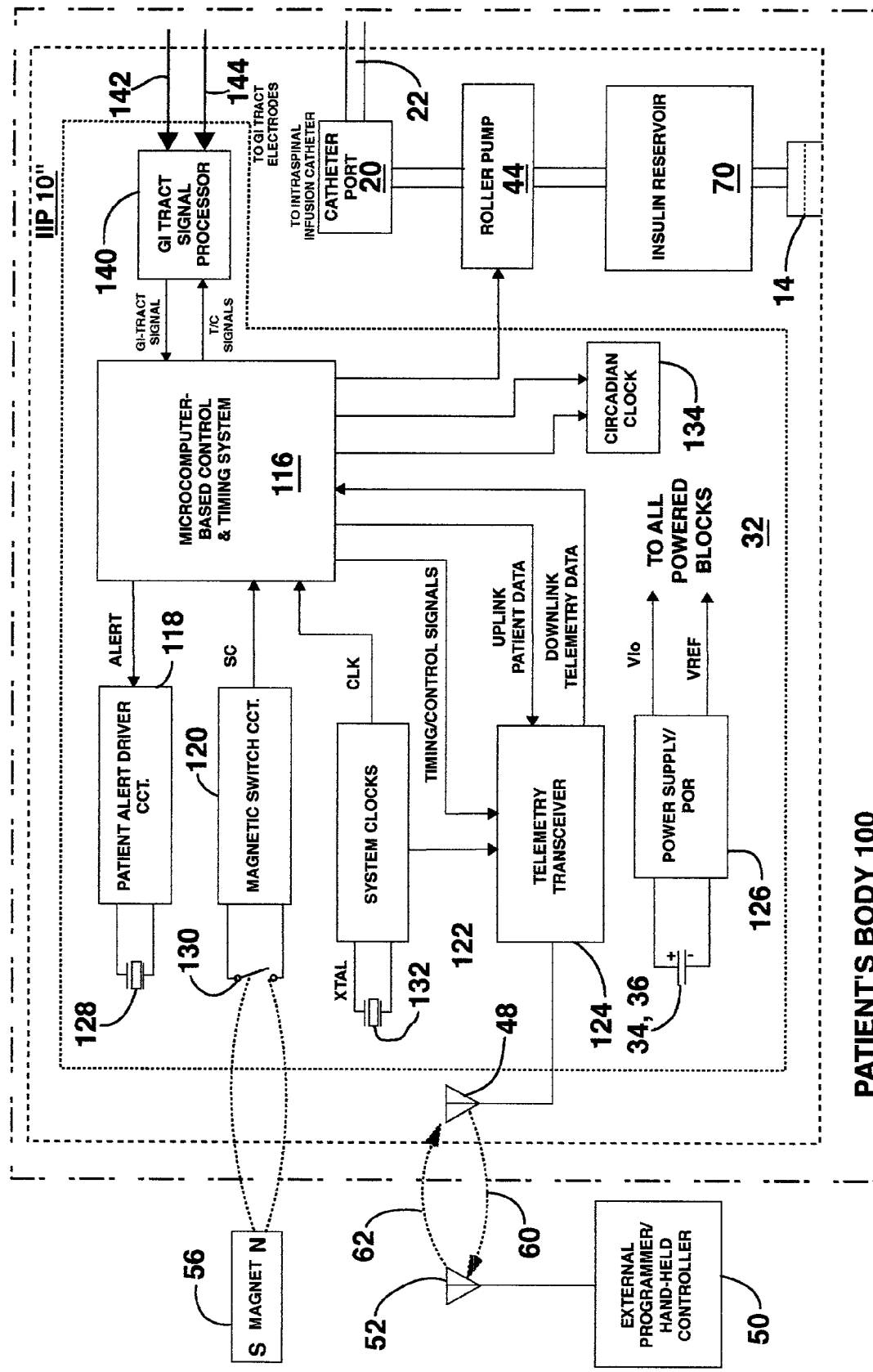
FIG. 10 is a block diagram of the components of the IIP of FIGS. 1–4 further incorporating monitoring circuitry and leads bearing electrodes implanted at selected sites of the stomach wall for developing a GI tract signal characteristic of peristalsis that triggers, in accordance with the second aspect of the invention, delivery of a drug into the intrathecal space by the IIP in accordance with the first aspect of the invention.
Figure 11:
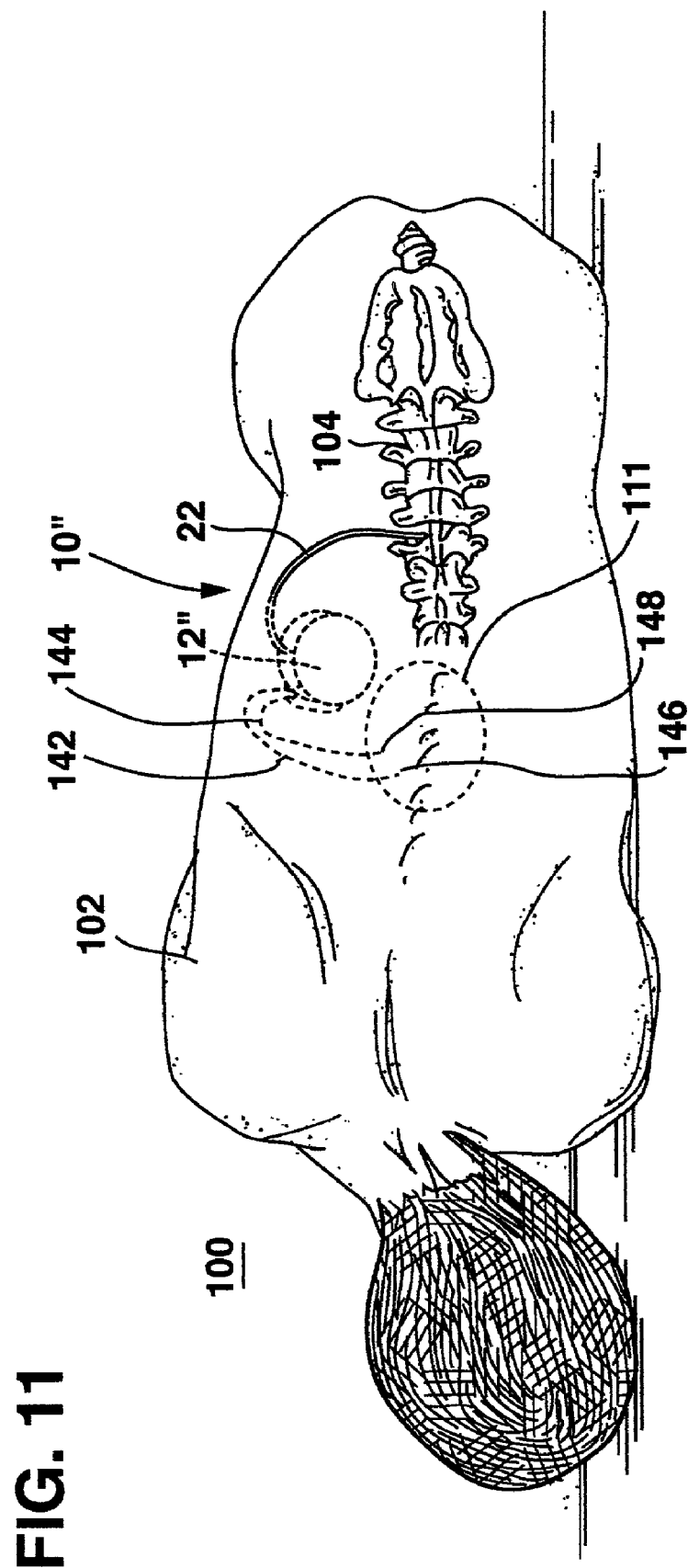
FIG. 11 schematically depicts the IIP of FIG. 10 implanted so that the intrathecal insulin delivery catheter extends into the intrathecal space and the GI tract leads extend to the sites of the stomach wall to develop the GI tract signal.

FIGS. 10 and 11 depict a further embodiment of an IIP'" combining the GI tract signals sensing functions of the GI tract stimulator/monitor 150 and the IIP 10' operating according to the steps of FIG. 12 as described above. In this embodiment, a GI tract signal processor 140 and a lead connector block are incorporated into the IIP 10'". GI tract leads 142 and 144 are electrically connected to the input of the GI tract signal processor 140 and extend from the IIP 10'" to respective electrodes 146 and 148 attached to wall of the stomach 111. The microcomputer-based control and timing system 116 generates timing and control signals that enable and set signal detection criteria of the GI tract signal processor 140. The GI tract signal is detected when the GI tract signal processor 140 is enabled after time-out of the delivery delay time in step S204 and when programmed spike potential detection criteria are met in step S206.

The patient can also be provided with the magnet 56 or hand-held controller 50 to separately initiate delivery of a dosage by IIP 10' or IIP'" if the delivery delay has timed out as per the steps of FIG. 7.

The second aspect of the invention conditioning delivery of a drug to treat obesity or other eating disorders upon the detection of the above-described spike potentials accompanying peristalsis can be practiced together with the first aspect of the invention as described above with respect to FIGS. 1–13. Or the second aspect of the invention can be practiced in conjunction with the IIP 10' or 10'' delivering the drug through a catheter 22' directly into the intercerebroventricular space 105 of the brain 103 to reach receptors in the brain controlling appetite as depicted particularly in FIG. 14. The IIP' 10 would operate in conjunction with the GI tract stimulator/monitor 150 and associated GI tract leads 154, 156 extending to GI tract sense electrodes implanted in the wall of the stomach 111 for developing a GI tract signal upon detection of the spike potentials of FIG. 13 characteristic of peristalsis in the same manner as described above with respect to FIGS. 8, 9, 12 and 13. Alternatively, the IIP 10'' would operate in conjunction with the GI tract leads 142, 144 extending to GI tract sense electrodes implanted in the wall of the stomach 111 for developing the GI tract signal upon detection of the spike potentials of FIG. 13 in the same manner as described above with respect to FIGS. 10–13.

This embodiment does not enjoy the less invasive procedure advantages of the first aspect of the invention, but does enjoy the advantages of the second aspect of the invention wherein delivery of the drug is tied more closely to the ingestion of food by the patient. Thus, it is necessary to bore through the skull and implant the distal extension 23 of catheter 22' into the intercerebroventricular space 105 to position the catheter port 25 proximal to the receptors of the brain 103 that respond to the delivered drug. Then, it is necessary to couple the distal extension 23 to the catheter 22' and route the catheter 22' subcutaneously to the remotely implanted IIP 10' or 10''. The catheter 22' and the distal extension 23 and the procedure of implantation are described in the above-referenced commonly assigned '990, '798 and '207 patents.

Generally speaking, sensing of EGG signals occurs between a pair of sense electrodes in this second aspect of the invention. While two GI tract leads 142, 144 and 154, 156 are depicted in the figures each supporting such a sense electrode, it will be understood that single leads carrying two spaced apart sense electrodes may be substituted for the separate leads or unipolar leads may be substituted for the separate leads wherein one sense electrode is at the case. Therefore, the expressions "GI tract leads" and "GI tract sense electrodes" embraces any and all such leads and electrodes.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical operation of the above described devices are not disclosed and are not necessary to the practice of the present invention. In addition, it will be understood that specifically described structures, functions and operations set forth in the above-referenced patents can be practiced in conjunction with the present invention, but they are not essential to its practice.

Thus, embodiments of INSULIN DELIVERY INTO CEREBRAL SPINAL FLUID FOR TREATMENT OF OBESITY are disclosed. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. A method of delivering drug from an implantable infusion pump to receptors of the brain to therapeutically treat an eating disorder of a patient by suppressing or enhancing appetite, the method comprising the steps of:
  surgically implanting an intrathecal drug infusion catheter so that a distal drug delivery portion lies in a predetermined intrathecal space site of the spinal column in cerebral spinal fluid (CSF) communication with receptors in the brain;
  coupling the proximal end of the drug infusion catheter to an drug infusion pump;
  implanting the drug infusion pump in the patient's body; and
  operating the pump to discharge a predetermined dosage of drug into the CSF sufficient to suppress or enhance appetite through interaction of drug transported through the CSF with receptors in the brain.

2. The method of claim 1, wherein the operating step further comprises:
providing the patient with an external medical device for communicating with the pump; and
utilizing the external medical device to communicate a command to the pump to discharge the predetermined dosage of drug into the CSF sufficient to suppress or enhance appetite through interaction with receptors in the brain.

3. The method of claim 2, wherein the operating step further comprises:
timing out a delay time from each discharge; and
inhibiting the pump from responding to the command if the delay time has not timed out.

4. The method of claim 1, wherein the drug is insulin acting to suppress appetite when detected by the receptors in the brain, and the operating step further comprises:
providing the patient with an external medical device for communicating with the pump; and
utilizing the external medical device to communicate a command to the pump to discharge a dosage of insulin in the range of $1 \times 10^{-5} - 15 \times 10^{-2}$ Units/Kg/day into the CSF sufficient to suppress appetite through interaction with receptors in the brain.

5. The method of claim 1, wherein the drug is insulin acting to suppress appetite when detected by the receptors in the brain, and the operating step further comprises:
providing the patient with an external medical device for communicating with the pump; and
utilizing the external medical device to communicate a command to the pump to discharge the predetermined dosage of insulin into the CSF sufficient to suppress or enhance appetite through interaction with receptors in the brain.

6. The method of claim 1, wherein the operating step further comprises:
timing out the time of day; and
operating the drug infusion pump at one or more predetermined time of day to discharge the predetermined dosage of drug into the CSF sufficient to suppress or enhance appetite through interaction with receptors in the brain.

7. The method of claim 1, wherein the drug is insulin acting to suppress appetite when detected by the receptors in the brain, and the operating step further comprises:
timing out the time of day; and
operating the pump at one or more predetermined time of day to discharge a dosage of insulin into the CSF sufficient to suppress appetite through interaction with receptors in the brain.

8. The method of claim 1, wherein the drug is insulin acting to suppress appetite when detected by the receptors in the brain, and the operating step further comprises:
timing out the time of day; and
operating the pump at one or more predetermined time of day to discharge a dosage of insulin in the range of $1 \times 10^{-5} - 15 \times 10^{-2}$ Units/Kg/day into the CSF sufficient to suppress appetite through interaction with receptors in the brain.

9. The method of claim 1, wherein the operating step further comprises the steps of:
detecting an electrical signal of the GI tract characteristic of peristalsis; and
triggering the operation of the drug infusion pump to discharge the predetermined dosage of drug into the CSF in timed relation to the detection of the electrical signal to suppress or enhance appetite through interaction with receptors in the brain.

10. The method of claim 9, wherein the operating step further comprises:
timing out a delay time from each discharge; and
inhibiting the pump from responding to the detection of the electrical signal of the GI tract if the delay time has not timed out.

11. The method of claim 9, wherein the detecting step further comprises the steps of:
implanting GI tract sense electrodes at predetermined sites of the GI tract traversed by electrical signals in the GI tract wall characteristic of peristalsis;
coupling the GI tract sense electrodes to GI tract sensing circuitry for detecting the electrical signals of the GI tract characteristic of peristalsis; and
triggering the operation of the drug infusion pump to discharge the predetermined dosage of drug into the CSF in timed relation to the detection of the electrical signals to suppress or enhance appetite through interaction with receptors in the brain.

12. The method of claim 11, wherein the GI tract sensing circuitry is located in the drug infusion pump.

13. The method of claim 9, wherein the detecting step further comprises the steps of:
implanting GI tract sense electrodes at predetermined sites of the GI tract traversed by electrical signals in the GI tract wall characteristic of peristalsis;
coupling the GI tract sense electrodes to GI tract sensing circuitry of a GI tract monitor for detecting the signals of the GI tract characteristic of peristalsis;
implanting the GI tract monitor in the patient's body;
operating the GI tract monitor to develop a GI tract signal upon detection of the signals of the GI tract characteristic of peristalsis;
transmitting the detected electrical signals of the GI tract to the drug infusion pump; and
triggering the operation of the drug infusion pump to discharge the predetermined dosage of drug into the CSF in timed relation to the detection of the electrical signals of the GI tract to suppress or enhance appetite through interaction with receptors in the brain.

14. The method of claim 13, wherein the drug is insulin acting to suppress appetite when detected by the receptors in the brain, and the operating step further comprises the steps of:
detecting an electrical signal of the GI tract characteristic of peristalsis; and
triggering the operation of the drug infusion pump to discharge a predetermined dosage of insulin into the CSF in timed relation to the detection of the electrical signal to suppress appetite through interaction with receptors in the brain.

15. The method of claim 9, wherein the drug is insulin acting to suppress appetite when detected by the receptors in the brain, and the operating step further comprises the steps of:
detecting an electrical signal of the GI tract characteristic of peristalsis; and
triggering the operation of the drug infusion pump to discharge a predetermined dosage of insulin into the CSF in timed relation to the detection of the electrical signal to suppress appetite through interaction with receptors in the brain.

16. The method of claim 9, wherein the drug is insulin acting to suppress appetite when detected by the receptors in the brain, and the operating step further comprises the steps of:
- detecting an electrical signal of the GI tract characteristic of peristalsis; and
- triggering the operation of the drug infusion pump to discharge a dosage of insulin in the range of $1\times10^{-5}$–$15\times10^{-2}$ Units/Kg/day into the CSF in timed relation to the detection of the electrical signal to suppress appetite through interaction with receptors in the brain.

17. A method of delivering drug from an implantable infusion pump to receptors of the brain to therapeutically treat an eating disorder of a patient by suppressing or enhancing appetite, the method comprising the steps of:
- surgically implanting an intrathecal drug infusion catheter so that a distal drug delivery portion lies in cerebral spinal fluid (CSF) in communication with receptors in the brain;
- coupling the proximal end of the drug infusion catheter to an drug infusion pump;
- implanting the drug infusion pump in the patient's body;
- detecting an electrical signal of the GI tract characteristic of peristalsis; and
- triggering the operation of the drug infusion pump to discharge the predetermined dosage of drug into the CSF in timed relation to the detection of the electrical signal to suppress or enhance appetite through interaction with receptors in the brain.

18. The method of claim 17, wherein the operating step further comprises:
- timing out a delay time from each discharge; and
- inhibiting the pump from responding to the detection of the electrical signal of the GI tract if the delay time has not timed out.

19. The method of claim 17, wherein the detecting step further comprises the steps of:
- implanting GI tract sense electrodes at predetermined sites of the GI tract traversed by electrical signals in the GI tract wall characteristic of peristalsis;
- coupling the GI tract sense electrodes to GI tract sensing circuitry for detecting the electrical signals of the GI tract characteristic of peristalsis; and
- triggering the operation of the drug infusion pump to discharge the predetermined dosage of drug into the CSF in timed relation to the detection of the electrical signals to suppress or enhance appetite through interaction with receptors in the brain.

20. The method of claim 19, wherein the GI tract sensing circuitry is located in the drug infusion pump.

21. The method of claim 17, wherein the detecting step further comprises the steps of:
- implanting GI tract sense electrodes at predetermined sites of the GI tract traversed by electrical signals in the GI tract wall characteristic of peristalsis;
- coupling the GI tract sense electrodes to GI tract sensing circuitry of a GI tract monitor for detecting the signals of the GI tract characteristic of peristalsis;
- implanting the GI tract monitor in the patient's body;
- operating the GI tract monitor to develop a GI tract signal upon detection of the signals of the GI tract characteristic of peristalsis;
- transmitting the detected electrical signals of the GI tract to the drug infusion pump; and
- triggering the operation of the drug infusion pump to discharge the predetermined dosage of drug into the CSF in timed relation to the detection of the electrical signals of the GI tract to suppress or enhance appetite through interaction with receptors in the brain.

22. The method of claim 17, wherein the drug is insulin acting to suppress appetite when detected by the receptors in the brain, and the triggering step further comprises triggering the operation of the drug infusion pump to discharge a predetermined dosage of insulin into the CSF in timed relation to the detection of the electrical signal to suppress appetite through interaction with receptors in the brain.

23. The method of claim 17, wherein the drug is insulin acting to suppress appetite when detected by the receptors in the brain, and the triggering step further comprises triggering the operation of the drug infusion pump to discharge a predetermined dosage of insulin in the range of $1\times10^{-5}$–$15\times10^{-2}$ Units/Kg/day into the CSF in timed relation to the detection of the electrical signal to suppress appetite through interaction with receptors in the brain.

24. A system comprising an implantable infusion pump for delivering drug to receptors of the brain to therapeutically treat an eating disorder of a patient by suppressing or enhancing the patient's appetite, the system comprising:
- an intrathecal drug infusion catheter having catheter lumen extending from a catheter proximal end and a distal drug infusion portion adapted to be implanted so that the distal drug delivery portion lies in a predetermined intrathecal space site of the spinal column in cerebral spinal fluid (CSF) in communication with receptors in the brain;
- a drug infusion pump comprising an drug reservoir, a pump and infusion discharge control circuitry adapted to be implanted in the patient and coupled to a proximal end of the drug infusion catheter, the infusion discharge control circuitry providing an infusion discharge control signal; and
- means responsive to an infusion discharge control signal of the infusion discharge control circuitry for initiating operation of the pump to discharge a predetermined dosage of drug into the cerebral spinal fluid (CSF) sufficient to suppress or enhance appetite through interaction of drug transported through the CSF with receptors in the brain, wherein the drug infusion discharge control circuitry comprises:
- means for detecting an electrical signal of the GI tract characteristic of peristalsis; and
- means for triggering the operation of the drug infusion pump to discharge the predetermined dosage of drug into the CSF in timed relation to the detection of the electrical signal to suppress or enhance appetite through interaction with receptors in the brain.

25. The system of claim 24, further comprising an external medical device operable by the patient or a medical care provider to generate an drug discharge command, and the drug infusion discharge control circuitry comprises:
- means for receiving and responding to the drug discharge command from the external medical device to develop the infusion discharge control signal; and
- means for timing out a delay time from each discharge; and
- means for inhibiting the pump from responding to the command if the delay time has not timed out.

26. The system of claim 24, further comprising an external medical device operable by the patient or a medical care provider to generate an drug discharge command, and the drug infusion discharge control circuitry comprises means for receiving and responding to the drug discharge command from the external medical device to develop the infusion discharge control signal.

27. The system of claim 26, wherein the drug is insulin acting to suppress appetite when detected by the receptors in the brain, and the triggering step further comprises triggering the operation of the drug infusion pump to discharge a predetermined dosage of insulin into the CSF in timed relation to the detection of the electrical signal to suppress appetite through interaction with receptors in the brain.

28. The system of claim 26, wherein the drug is insulin acting to suppress appetite when detected by the receptors in the brain, and the triggering step further comprises triggering the operation of the drug infusion pump to discharge a predetermined dosage of insulin in the range of $1 \times 10^{-5}$–$15 \times 10^{-2}$ Units/Kg/day into the CSF in timed relation to the detection of the electrical signal to suppress appetite through interaction with receptors in the brain.

29. The system of claim 26, wherein the drug infusion discharge control circuitry comprises:
   means for timing out the time of day; and
   means for operating the drug infusion pump at one or more predetermined time of day to discharge the predetermined dosage of drug into the CSF sufficient to suppress or enhance appetite through interaction with receptors in the brain.

30. The system of claim 29, wherein the drug is insulin acting to suppress appetite when detected by the receptors in the brain, and the triggering step further comprises triggering the operation of the drug infusion pump to discharge a predetermined dosage of insulin into the CSF in timed relation to the detection of the electrical signal to suppress appetite through interaction with receptors in the brain.

31. The system of claim 29, wherein the drug is insulin acting to suppress appetite when detected by the receptors in the brain, and the triggering step further comprises triggering the operation of the drug infusion pump to discharge a predetermined dosage of insulin in the range of $1 \times 10^{-5}$–$15 \times 10^{-2}$ Units/Kg/day into the CSF in timed relation to the detection of the electrical signal to suppress appetite through interaction with receptors in the brain.

32. The system of claim 24, wherein the drug is insulin acting to suppress appetite when detected by the receptors in the brain.

33. The system of claim 24, wherein the drug infusion discharge control circuitry comprises:
   means for timing out a delay time from each discharge; and
   means for inhibiting the pump from responding to the detection of the electrical signal of the GI tract if the delay time has not timed out.

34. The system of claim 24, wherein the means for detecting an electrical signal of the GI tract characteristic of peristalsis comprises:
   GI tract sense electrodes adapted to be implanted at predetermined sites of the GI tract traversed by electrical signals in the GI tract wall characteristic of peristalsis; and
   GI tract sensing circuitry coupled with the GI tract sense electrodes for detecting the electrical signals of the GI tract characteristic of peristalsis.

35. The system of claim 34, wherein the GI tract sensing circuitry is located in the drug infusion pump.

36. The system of claim 24, further comprising:
   GI tract leads bearing a sense electrodes adapted to be implanted at predetermined sites of the GI tract traversed by electrical signals in the GI tract wall characteristic of peristalsis; and
   a GI tract monitor adapted to be implanted in the patient's body and coupled to the GI tract leads sense electrodes and further comprising:
      means for developing a GI tract signal upon detection of the signals of the GI tract characteristic of peristalsis; and
      means for transmitting the detected electrical signals of the GI tract to the drug infusion pump; and wherein:
   the drug infusion discharge control circuitry further comprises means for receiving the transmitted electrical signals of the GI tract.

37. A system comprising an implantable infusion pump for delivering drug to receptors of the brain to therapeutically treat an eating disorder of a patient by suppressing or enhancing the patient's appetite, the system comprising:
   an intrathecal drug infusion catheter having catheter lumen extending from a catheter proximal end and a distal drug infusion portion adapted to be implanted so that the distal drug delivery portion lies in a predetermined intrathecal space site of the spinal column in cerebral spinal fluid (CSF) in communication with receptors in the brain;
   a drug infusion pump comprising an drug reservoir, a pump and infusion discharge control circuitry adapted to be implanted in the patient and coupled to a proximal end of the drug infusion catheter, the infusion discharge control circuitry providing an infusion discharge control signal; and
   means responsive to an infusion discharge control signal of the infusion discharge control circuitry for initiating operation of the pump to discharge a predetermined dosage of drug into the cerebral spinal fluid (CSF) sufficient to suppress or enhance appetite through interaction of drug transported through the CSF with receptors in the brain, and
   wherein the drug is insulin acting to suppress appetite when detected by the receptors in the brain, and the operating step further comprises:
   means for detecting an electrical signal of the GI tract characteristic of peristalsis; and
   means for triggering the operation of the drug infusion pump to discharge a predetermined dosage of insulin in the range of $1 \times 10^{-5}$–$15 \times 10^{-2}$ Units/Kg/day into the CSF in timed relation to the detection of the electrical signal to suppress appetite through interaction with receptors in the brain.

38. A system delivering drug from an implantable infusion pump to receptors of the brain to therapeutically treat an eating disorder of a patient by suppressing or enhancing appetite comprising:
   a drug infusion catheter having catheter lumen extending from a catheter proximal end and a distal drug infusion portion adapted to be implanted so that the distal drug delivery portion lies in cerebral spinal fluid (CSF) in communication with receptors in the brain;
   a drug infusion pump comprising an drug reservoir, a pump, and infusion discharge control circuitry adapted to be implanted in the patient and coupled to a proximal end of the drug infusion catheter;
   means for detecting an electrical signal of the GI tract characteristic of peristalsis; and
   means for triggering the operation of the drug infusion pump to discharge the predetermined dosage of drug into the CSF in timed relation to the detection of the electrical signal to suppress or enhance appetite through interaction with receptors in the brain.

39. The system of claim 38, wherein the drug is insulin acting to suppress appetite when detected by the receptors in the brain, and the triggering means further comprises means for triggering the operation of the drug infusion pump to discharge a predetermined dosage of insulin in the range of $1\times10^{-5}$–$15\times10^{-2}$ Units/Kg/day into the CSF in timed relation to the detection of the electrical signal to suppress appetite through interaction with receptors in the brain.

40. The system of claim 38, further comprising:
   means for timing out a delay time from each discharge; and
   means for inhibiting the pump from responding to the detection of the electrical signal of the GI tract if the delay time has not timed out.

41. The system of claim 38, wherein the detecting means further comprises:
   GI tract sensing circuitry for detecting the electrical signals of the GI tract characteristic of peristalsis
   GI tract sense electrodes adapted to be implanted at predetermined sites of the GI tract traversed by electrical signals in the GI tract wall characteristic of peristalsis; and
   GI tract leads coupling the GI tract sense electrodes to the GI tract sensing circuitry.

42. The system of claim 41, wherein the GI tract sensing circuitry is located in the drug infusion pump.

43. The system of claim 38, wherein the detecting means further comprises:
   GI tract leads having GI tract sense electrodes adapted to be implanted at predetermined sites of the GI tract traversed by electrical signals in the GI tract wall characteristic of peristalsis; and
   a GI tract monitor adapted to be implanted in the patient's body comprising:
     GI tract sensing circuitry coupled to the GI tract leads for detecting the electrical signals of the GI tract characteristic of peristalsis; and
     means for transmitting the detected electrical signals of the GI tract to the drug infusion pump.

44. The system of claim 38, wherein the drug is insulin acting to suppress appetite when detected by the receptors in the brain, and the triggering means further comprises means for triggering the operation of the drug infusion pump to discharge a predetermined dosage of insulin into the CSF in timed relation to the detection of the electrical signal to suppress appetite through interaction with receptors in the brain.

* * * * *